US011364675B2

(12) United States Patent
Nordgren

(10) Patent No.: US 11,364,675 B2
(45) Date of Patent: Jun. 21, 2022

(54) PRINTING METHOD FOR THERMOPLASTIC RETENTION DEVICE PREFORM

(71) Applicant: Medtec, Inc., Orange City, IA (US)

(72) Inventor: Gregory Nordgren, Saratoga Springs, UT (US)

(73) Assignee: MEDTEC LLC, Orange City, IA (US)

( * ) Notice: Subject to any disclaimer, the term of this patent is extended or adjusted under 35 U.S.C. 154(b) by 156 days.

(21) Appl. No.: 16/341,986

(22) PCT Filed: Sep. 13, 2017

(86) PCT No.: PCT/US2017/051347
§ 371 (c)(1),
(2) Date: Apr. 15, 2019

(87) PCT Pub. No.: WO2018/084935
PCT Pub. Date: May 11, 2018

(65) Prior Publication Data
US 2019/0248066 A1  Aug. 15, 2019

Related U.S. Application Data

(60) Provisional application No. 62/415,662, filed on Nov. 1, 2016.

(51) Int. Cl.
B29C 64/118 (2017.01)
B33Y 80/00 (2015.01)
(Continued)

(52) U.S. Cl.
CPC ............ B29C 64/118 (2017.08); B33Y 70/00 (2014.12); B33Y 80/00 (2014.12); A61B 90/18 (2016.02);
(Continued)

(58) Field of Classification Search
CPC .............................. B29C 64/118; B33Y 70/00
See application file for complete search history.

(56) References Cited

U.S. PATENT DOCUMENTS 5,926,388 A  7/1999  Kimbrough et al.
6,564,086 B2  5/2003  Marchitto et al.
(Continued)

FOREIGN PATENT DOCUMENTS

WO  2013093843 A1  6/2013
WO  2016108154 A1  7/2016

OTHER PUBLICATIONS

International Search Report and Written Opinion issued in corresponding International Application No. PCT/US2017/051347, dated Nov. 29, 2017, 14 pages.

*Primary Examiner* — Nicholas R Krasnow
(74) *Attorney, Agent, or Firm* — Snyder, Clark, Lesch & Chung, LLP

(57) ABSTRACT

A method for forming a preform for a thermoplastic retention device is provided. The method includes providing a thermoplastic base material and blending the base material with one or more chemical agents to form a polymer blend. The chemical agents are configured to modify a polymer chain of the base material when the polymer blend is exposed to radiation. The method further includes forming the polymer blend into a filament sized for a three-dimensional printing platform and printing a preform shape from the filament using the three-dimensional printing platform. After the printed preform is hardened, the method includes exposing the printed preform shape to radiation sufficient to cause a reaction between the one or more chemical agents and the base material.

17 Claims, 8 Drawing Sheets

(51) Int. Cl.
  *B33Y 70/00*    (2020.01)
  *B29C 35/08*    (2006.01)
  *A61N 5/10*     (2006.01)
  *A61B 90/10*    (2016.01)
  *B33Y 10/00*    (2015.01)
  *A61B 90/18*    (2016.01)
  *B29K 67/00*    (2006.01)

(52) U.S. Cl.
  CPC . *A61B 2090/101* (2016.02); *A61N 2005/1097* (2013.01); *B29C 2035/085* (2013.01); *B29K 2067/04* (2013.01); *B33Y 10/00* (2014.12)

(56) References Cited

U.S. PATENT DOCUMENTS

| | | |
|---|---|---|
| 7,968,026 B1 | 6/2011 | Teoh et al. |
| 8,071,007 B1 | 12/2011 | Teoh et al. |
| 8,320,648 B2 | 11/2012 | Mailling et al. |
| 8,859,691 B2 | 10/2014 | Zhang |
| 8,861,800 B2 | 10/2014 | Savvides et al. |
| 2001/0044668 A1 | 11/2001 | Kimbrough et al. |
| 2005/0280184 A1 | 12/2005 | Sayers et al. |
| 2007/0156141 A1* | 7/2007 | Cuypers ............... A61B 90/14 606/54 |
| 2009/0101278 A1* | 4/2009 | Laberge-Lebel ...... B29C 64/106 156/275.5 |
| 2014/0209098 A1 | 7/2014 | Dunn et al. |
| 2014/0356585 A1* | 12/2014 | Duoss ..................... B32B 5/26 428/174 |
| 2015/0000679 A1* | 1/2015 | Cuypers ............... A61F 5/3707 128/869 |
| 2015/0102526 A1 | 4/2015 | Ward et al. |
| 2015/0157822 A1 | 6/2015 | Karpas et al. |
| 2015/0265794 A1 | 9/2015 | De Kruyff et al. |
| 2016/0067375 A1 | 3/2016 | Holmes et al. |
| 2016/0107379 A1 | 4/2016 | Mark et al. |
| 2016/0159009 A1* | 6/2016 | Canale .................. B33Y 10/00 264/401 |
| 2016/0200047 A1 | 7/2016 | Mark et al. |
| 2017/0253681 A1* | 9/2017 | Shen ....................... C08K 3/011 |
| 2017/0332733 A1* | 11/2017 | Cluckers ................ A43B 7/141 |
| 2018/0001547 A1* | 1/2018 | Cuypers ................ B33Y 70/00 |
| 2018/0098919 A1* | 4/2018 | Pallari .................. A61K 8/0212 |
| 2018/0257266 A1* | 9/2018 | Cook .................... B29C 70/347 |

\* cited by examiner

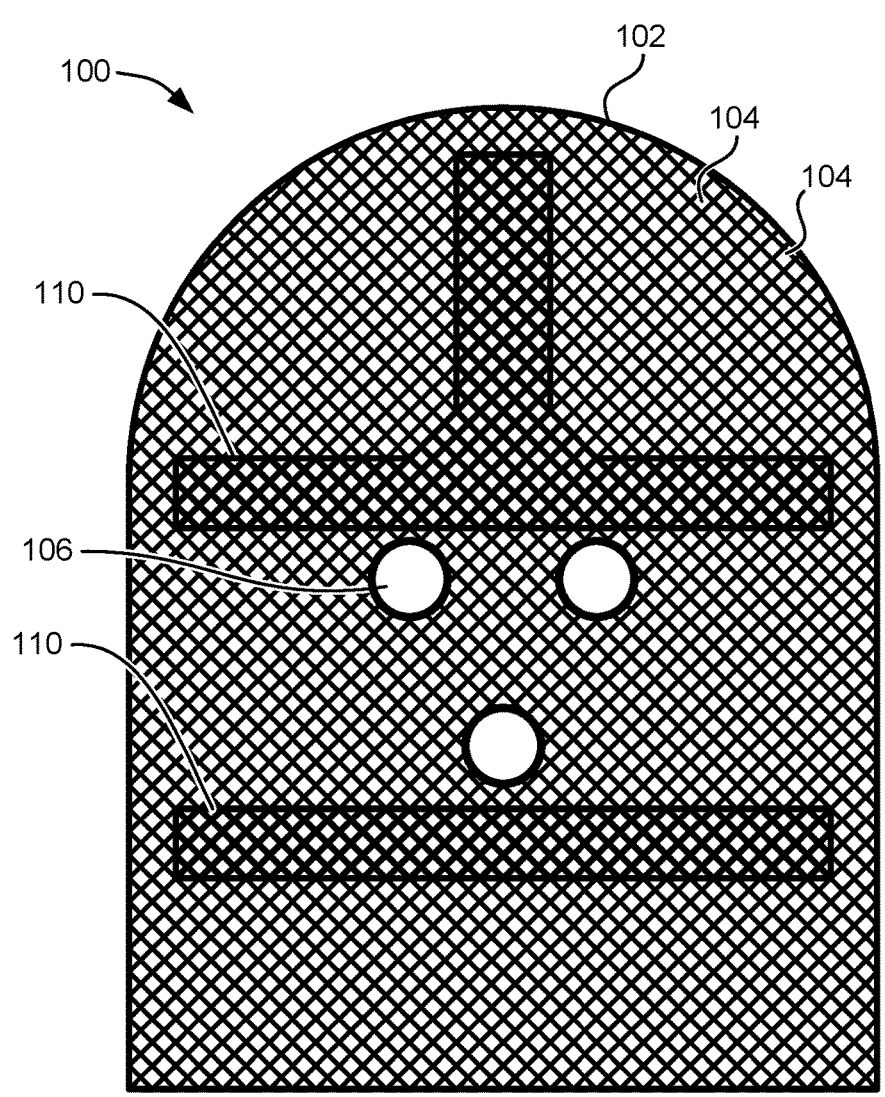
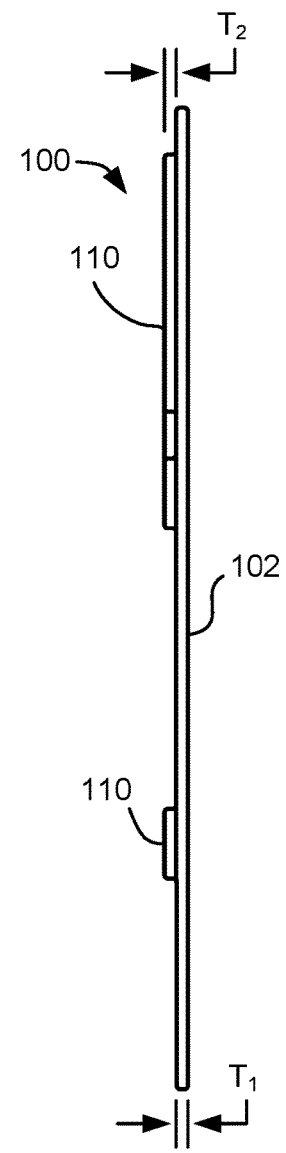
FIG. 1A
FIG. 1B
FIG. 1C

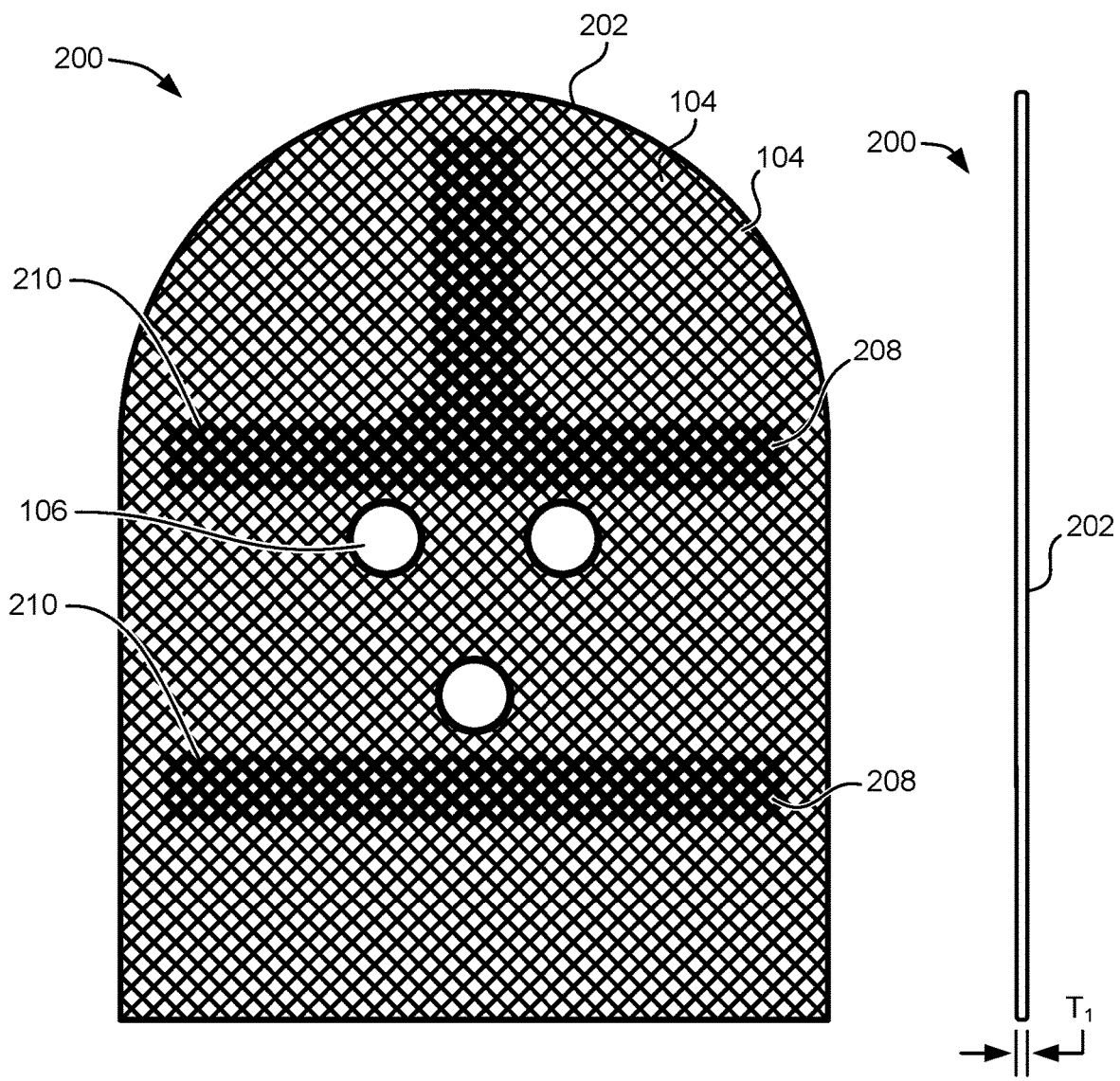

FIG. 3A
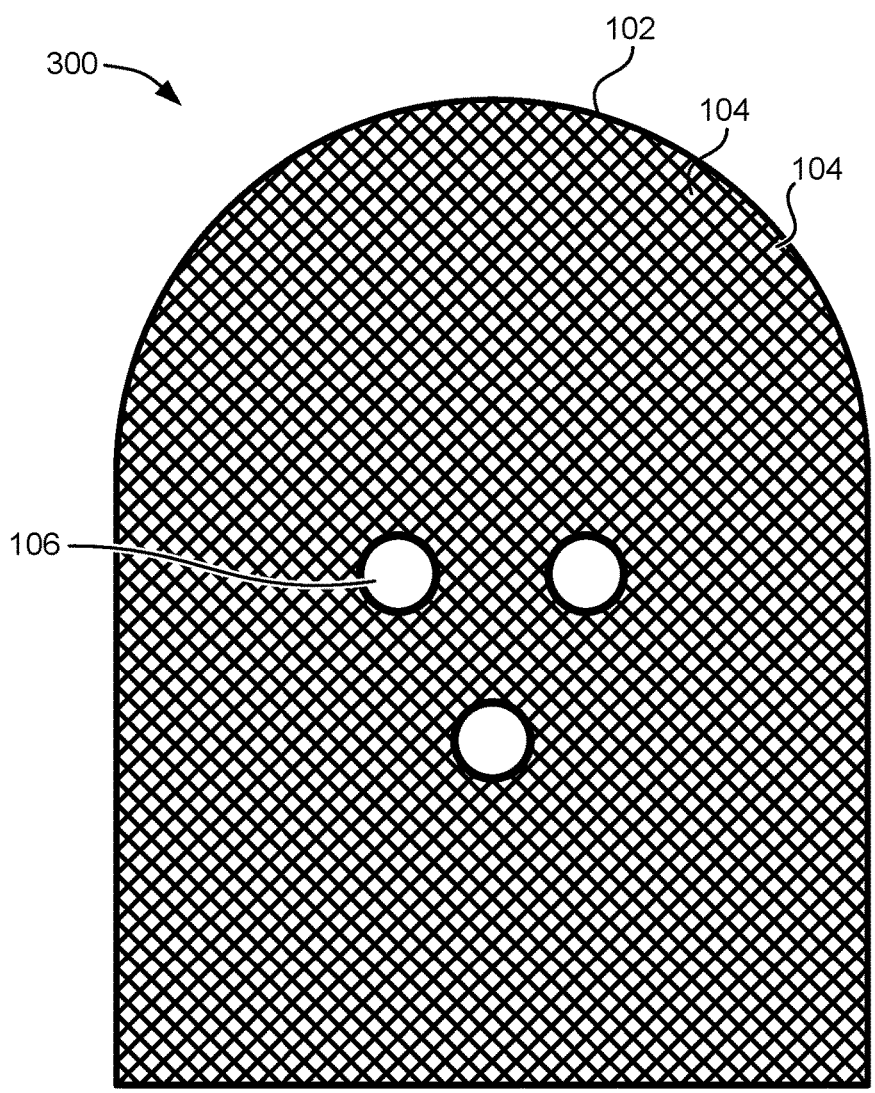
FIG. 3B
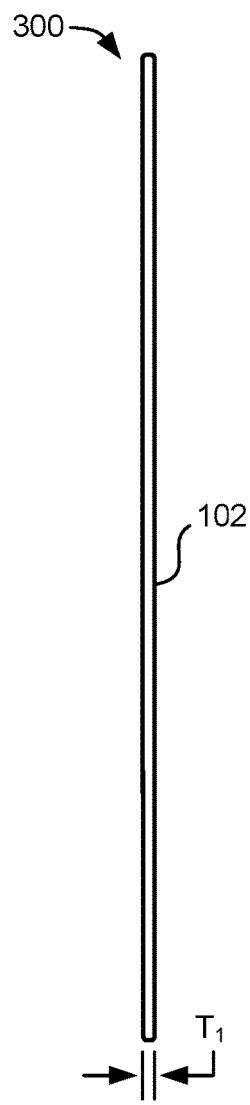
FIG. 3C

PRINTING METHOD FOR THERMOPLASTIC RETENTION DEVICE PREFORM

This application claims priority under 35 U.S.C. § 119, based on U.S. Provisional Patent Application No. 62/415,662 filed Nov. 1, 2016, the disclosure of which is hereby incorporated by reference herein.

BACKGROUND OF THE INVENTION

The present invention relates to forming the preform of a thermoplastic retention device.

For patients undergoing multiple radiation treatments, treated body parts must be in the same location every time so that the targeted area is also in the same place for treatment. Custom-fitting retention devices are used to ensure that a particular position can be repeated. For example, radiation oncology practices use heat-formable, polymer masks made from preform shapes that are stretched over a patient's face. A hot water bath or oven is employed to heat the mask preform, which is then formed over the patient. When a mask cools, it is permanently formed to the facial features of the patient. The preform material, however, is expensive and the mask consists of relatively thick material that can be difficult to stretch.

BRIEF DESCRIPTION OF THE DRAWINGS

FIGS. 1A-1C are top, front, and side views, respectively, of a thermoplastic retention device preform, according to an implementation described herein;

FIGS. 2A-2C are top, front, and side views, respectively, of a thermoplastic retention device preform, according to another implementation described herein;

FIGS. 3A-3C are top, front, and side views, respectively, of a thermoplastic retention device preform, according to still another implementation described herein;

DETAILED DESCRIPTION OF THE PREFERRED EMBODIMENTS

Figure 4A:
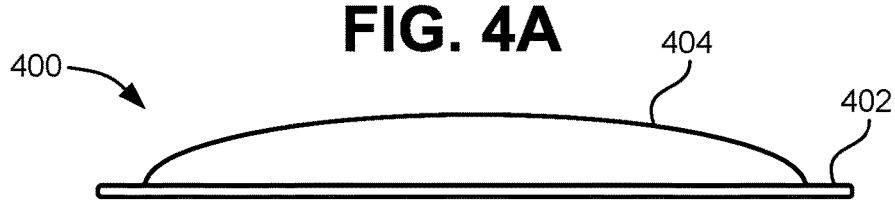
FIG. 4A-4C are top, front, and side cross-sectional views, respectively, of a thermoplastic retention device preform, according to yet another implementation described herein.

The following detailed description refers to the accompanying drawings. The same reference numbers in different drawings may identify the same or similar elements.

In the medical industry when radiation therapy is used, it is sometimes needed to restrain a certain body part during the procedure. A thermoplastic material is used to help create a form over the body part needing restraint. The thermoplastic material softens when heated and hardens when it cools back to room temperature. The thermoplastic material is provided to medical customers as a preform. The preform is connected to a rigid (e.g., non-thermoplastic) frame. The frame with the preform is typically sized to be positioned over a body part such that the preform can be pressed down onto the body part. After the thermoplastic material is heated, the frame with the preform is pressed over the body part, conforming the preform to the body part shape. The preform cools and retains the formed shape. The preform material has particular properties that are desired for creating a customized restraint, which include chemical promotion of a base polymer to enhance the crosslinking of the polymer when exposed to radiation.

Preforms preferably include different patterns which may provide advantages to medical technicians and patients. The patterns include an overall shape (e.g., a head shape, a head/neck/shoulders shape, a hip/pelvis shape, a torso shape, etc.) and also areas of different pattern density/strength may be needed to provide structural integrity while minimizing weight. In some cases, different hole or perforation patterns are used within a single preform. The holes or perforations may be added, for example, in low stress areas to reduce the overall weight of a preform/mask and to provide the impression of a less confining environment for a patient.

Using current practices, preforms are formed from molded or extruded sheets of a thermoplastic material that have been exposed to radiation to promote crosslinking. The sheets are then formed into preform patterns to particular customer specifications. Expensive and specialized equipment is needed to mold or extrude the base material into sheets, and even more specialized equipment is needed to cut and form these sheets into the desired shapes and hole patterns. Furthermore, changes to the configuration of the preform shape require tooling to cut or form the new shape.

According to implementations described herein, a method for forming a preform for a thermoplastic retention device is provided. The method includes providing a thermoplastic base material and blending the base material with one or more chemical agents to form a polymer blend. The chemical agents are configured to modify a polymer chain of the base material when the polymer blend is exposed to radiation. The method further includes forming the polymer blend into a filament sized for a three-dimensional printing platform and printing a preform shape from the filament using the three-dimensional printing platform. After the printed preform is hardened, the method includes exposing the printed preform shape to radiation that is sufficient to cause a reaction between the chemical agents and the base material. The radiated polymer blend creates a "memory" in the preform material. When the material is later heated to a softening temperature (e.g., in a warm water bath), the preform can be shaped (e.g., around a body part of patient) without losing integrity and will maintain its shape once cooled.

According to another implementation, a method for forming a preform for a thermoplastic retention incudes providing a thermoplastic base material; blending the base material with one or more chemical agents to form a polymer blend, the one or more chemical agents being configured to modify a polymer chain of the base material when the polymer blend is exposed to radiation; forming the polymer blend into a filament sized for a three-dimensional printing platform; exposing the filament to radiation sufficient to cause a reaction between the one or more chemical agents and the base material; and printing a preform shape from the filament using the three-dimensional printing platform. Exposing the filament to radiation may include exposing the filament to between 0.1 to 1.0 Megarads of gamma radiation.

As used herein, the term "thermoplastic" refers to heat-moldable thermoplastic materials, including medical-grade thermoplastic materials.

FIGS. 1A-1C are top, front, and side views, respectively, of a thermoplastic retention device preform 100 according to an implementation. In the configuration of FIGS. 1A-1C, preform 100 may correspond to a face mask. However, in other implementations, preform shapes for other body parts or combinations of body parts may be used. Preform 100 may include a generally flat base layer 102 of thermoplastic material. It is often desirable to minimize the amount of thermoplastic material used in each preform to reduce material costs, reduce weight, and provide a formed restraint with a more open feel for the patient. For example, base layer 102 may include holes 104 (or a lattice-type structure) to decrease the overall mass of preform 100. Larger openings 106 may also be included to provide access to or openings for a patient. Holes 104 and openings 106 in base layer 102 may extend through a thickness $T_1$ of base layer 102 and may weaken the overall strength of base layer 102. Thus, in the configuration of FIGS. 1A-1C, strategically placed reinforcement areas 110 may be used to strengthen areas of likely stress in base layer 102. Reinforcement areas 110 may strengthen preform 100 by providing areas of additional thickness ($T_2$) to base layer 102. In one implementation, the thickness $T_1$ of base layer 102 may be between 2 to 4 millimeters (mm). Reinforcement areas 110 may add additional thickness ($T_2$) of 1 to 3 mm. In one implementation, the thickness $T_2$ of preform 100 at reinforcement area 110 may be double the thickness $T_1$ of base layer 102.

FIGS. 2A-2C are top, front, and side views, respectively, of a thermoplastic retention device preform 200, according to another implementation. Similar to preform 100 described above, preform 200 may correspond to a face mask. Preform 200 may include a generally flat base layer 202 of thermoplastic material with holes 104 and openings 106 extending through a thickness $T_1$ of base layer 202. Similar to preform 100 described above, reinforcement areas 210 are provide to strengthen areas of likely stress in base layer 202. However, in contrast with reinforcement areas 110 above, reinforcement areas 210 may strengthen preform 100 by providing areas of increased density compared to base layer 102. For example, reinforcement areas 210 may include smaller holes 208 (compared to holes 104) or no holes. Thus, preform 200 may have varying density with a consistent thickness $T_1$ throughout.

FIGS. 3A-3C are top, front, and side views, respectively, of a thermoplastic retention device preform 300, according to still another implementation. Similar to preforms 100 and 200 described above, preform 300 may correspond to a face mask. Preform 300 may include generally flat base layer 102 with holes 104 and openings 106 extending through thickness $T_1$ of base layer 102. In contrast with preforms 100 and 200 described above, no reinforcement areas are included in preform 300.

Figure 4B:
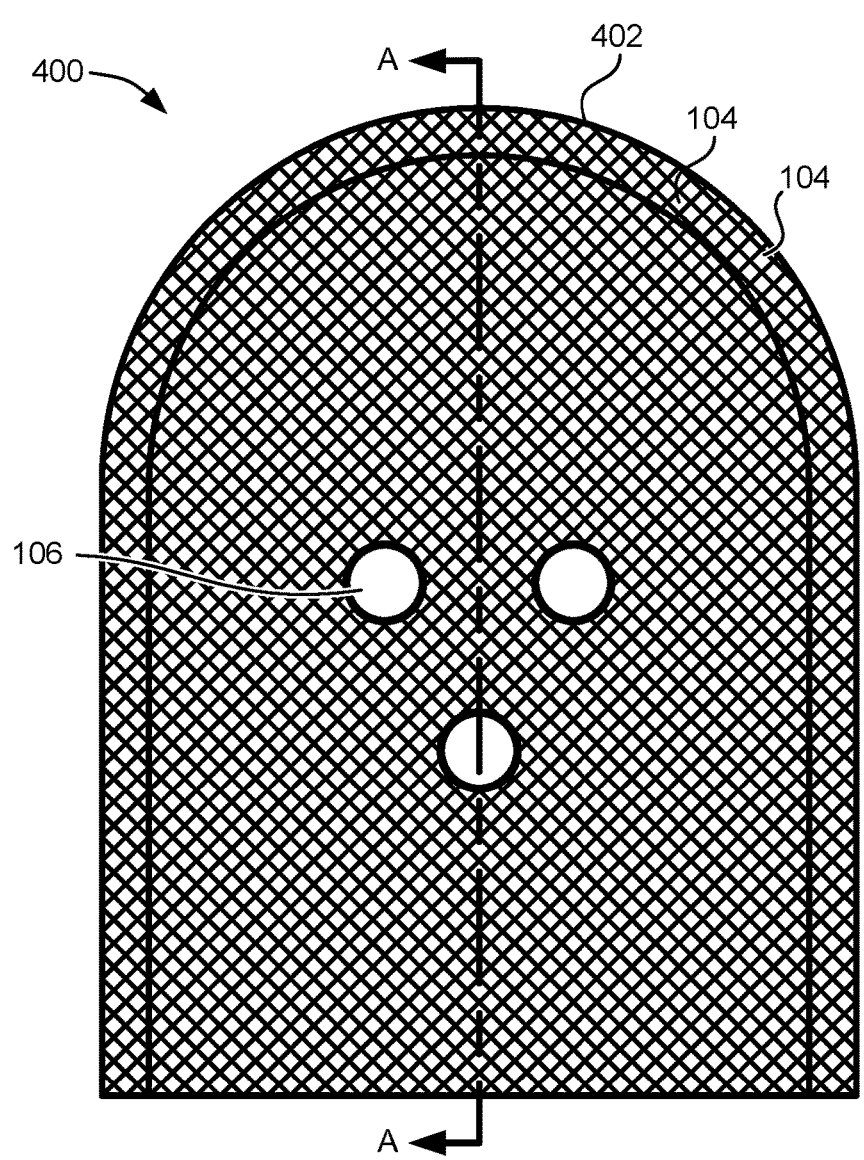
Figure 4C:
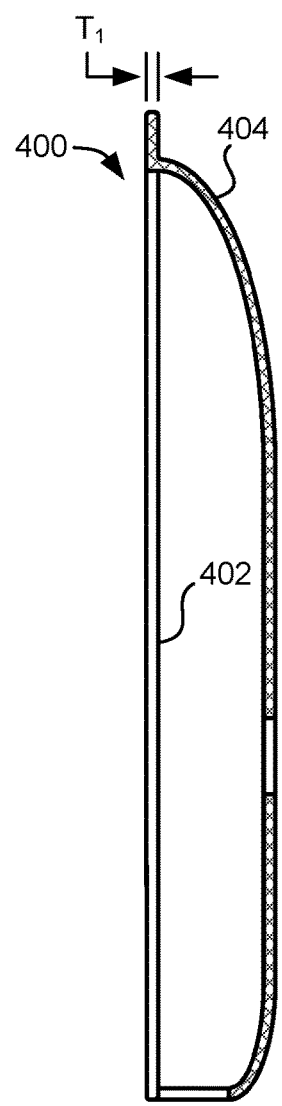

FIGS. 4A and 4B are top and front views, respectively, of a thermoplastic retention device preform 400, according to yet another implementation. FIG. 4C is a side cross-sectional view of preform 400 along section A-A of FIG. 4B. Similar to preforms 100, 200, and 300 described above, preform 400 may correspond to a face mask. Preform 400 may include a generally flat support layer 402 and a substantially dome-shaped portion 404. Each of support layer 402 and substantially dome-shaped portion 404 may include holes 104 extending through a thickness $T_1$. Support layer 402 may provide a surface for attachment of a frame. Substantially dome-shaped portion 404 may include larger openings 106 and may correspond to a partially-formed shape of a body part (e.g., a human head). Thus, in comparison with a flat preform (e.g., preforms 100, 200, and 300), preform 400 with the substantially dome-shaped portion 404 would require less deformation to conform to the body part of a patient. In other implementations, substantially dome-shaped portion 404 may be configured with a different three-dimensional, contoured (e.g., non-flat) profile. For example, substantially dome-shaped portion 404 may be configured to indicate general placement of preform 400 over a particular body feature, such as an indentation (or projection) for a nose or multiple indentations (or projections) for individual fingers. In the example of FIGS. 4A-4C, preform 400 is shown with a generally consistent thickness and density. In other implementations, preform 400 may incorporate different thicknesses or portions with different densities, as described above with respect to preforms 100 and 200.

Figure 5:
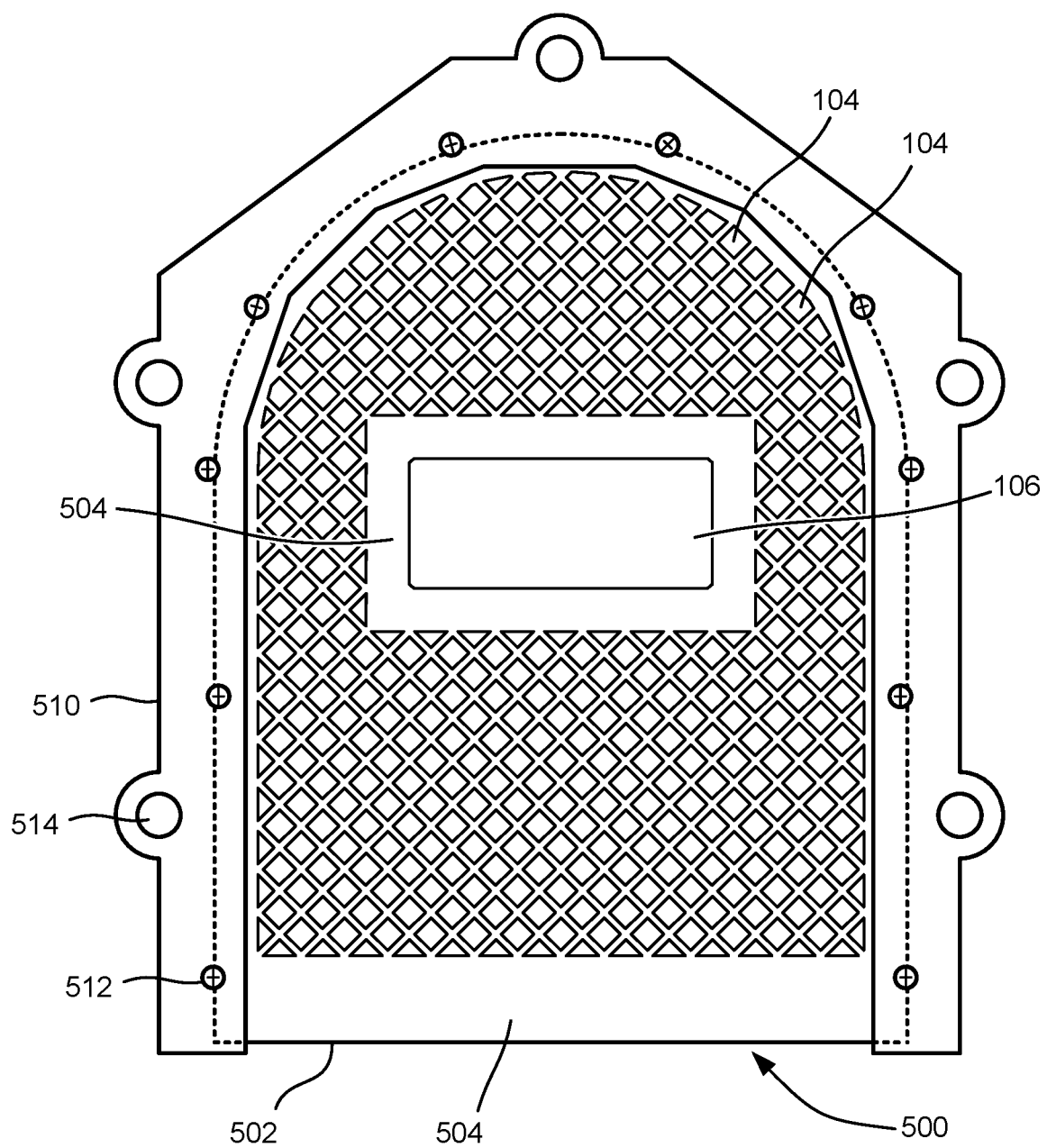
FIG. 5 is a front view of a thermoplastic retention device preform mounted in a frame, according to an implementation described herein.

FIG. 5 is a front view of a thermoplastic retention device preform 500 secured to a frame 510, according to another implementation. Similar to preforms 100, 200, 300, and 400 described above, preform 500 may correspond to a face mask. Preform 500 may include a generally flat base layer 502 of thermoplastic material with holes 104 and an opening 106 extending through a thickness of base layer 502. Base layer 502 may include one or more solid portions 504 to provide reinforcement and/or a surface for attachment to frame 510. Frame 510 may include a relatively rigid structure that may be mechanically fastened, glued, or otherwise secured to preform 500. As shown in the example of FIG. 5, frame 510 may be a two-piece structure secured over portions of preform 500 (e.g., solid portions 504) using screws 512. Frame 510 may include mounting holes 514 to enable frame 510 to be secured to a table or another surface (e.g., after preform 500 has been placed and/or formed over a patient's head).

According to implementations described herein, each of preforms 100, 200, 300, 400, and 500 described above may be manufactured using the same or similar basic methods and equipment. For example, a base polymer of polycaprolactone (PCL) may be treated with chemicals before use in making any preform. The chemical treatment enhances the crosslinking of the polymer chains within the polymer when later exposed to radiation. After applying the chemical treatment, but before exposing the treated base polymer to radiation, the polymer blend is extruded as a filament for a three-dimensional (3D) printing platform or printer. Using the filament, the 3D printer may apply a computer-aided design (CAD) model to create the desired preform shape (such as one of preforms 100, 200, 300, 400, and 500). After printing the preform, radiation is applied to the preform. The radiated polymer blend creates a memory in the material that allows the material to retain a shape when cool. When the material is later heated to a softening temperature (e.g., in a warm water bath at about 60° C.), the preform can be shaped (e.g., around a body part of patient) without losing integrity and will maintain its shape once cooled.

Current production methods of making thermoplastic preforms use sheets of preform material (e.g., with consistent thickness and density), which requires cutting out shapes and adding holes to make the preform. In contrast, implementations described herein provide cost advantages, flexibility, and production of shapes that are difficult or impossible achieve with current methods. However, processing of thermoplastic material (e.g., PCL) through 3D printing machines requires more than a simple substation of conventional 3D plastic filaments, such as PLA (Polylactic Acid) or ABS (Acrylonitrile Butadiene Styrene).

Figure 6:
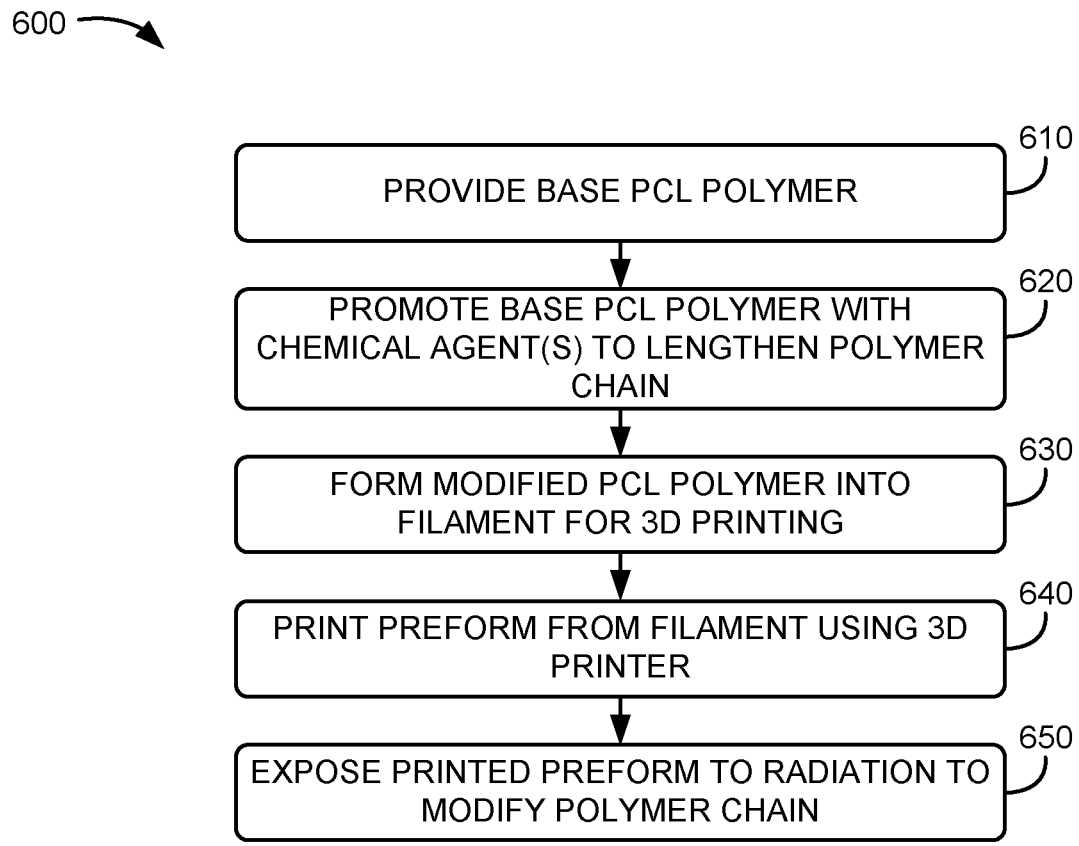
FIG. 6 is a flow diagram of an exemplary process for producing a thermoplastic retention device preform, according to an implementation described herein.

FIG. 6 is a flow diagram of a process 600 for producing a thermoplastic retention device preform, according to an implementation described herein. Process 600 may include providing a base PCL polymer (block 610). For example, the base PCL polymer may include a high molecular weight thermoplastic linear polyester suitable for use in positioning and immobilization of a patient. In one implementation, the base PCL polymer may be a 50,000 MW (mean molecular weight) linear thermoplastic PCL diol polymer, such as CAPA 6500C manufactured by Perstorp Holding AB, Malmo, Sweden. The base PCL polymer may be supplied, for example, in a granular (or pelletized) form.

Process 600 may further include promoting the base PCL polymer with one or more chemical agents to lengthen the polymer chain (block 620). For example, one or more crosslinking agents may be used to eventually modify (e.g., lengthen) the polymer chain of the base PCL polymer. In one implementation, the crosslinking agents may include two trifunctional monomers. One preferred crosslinking agent is triallylcyanurate, available from Sartomer Corp., Exton, Pa., USA as SR507A. Another preferred crosslinking agent that may be used is trimethylolpropane trimethacrylate, also available from Sartomer Corp. as SR350. In one implementation, equal amounts of each crosslinking agent may be mixed with the base PCL polymer. For example, the amount of crosslinking agent may generally be about 0.2 to 2 parts by weight per 100 parts PCL polymer, and preferably 1 part per hundred. Thus, an exemplary copolymer composition may be 100 parts PCL, 0.5 parts triallylcyanurate, and 0.5 parts trimethylolpropane trimethacrylate by weight. In one implementation, the crosslinking agents may be mixed with the base PCL polymer by mixing and heating the combined composition at an elevated temperature (e.g., above the melting temperature of the base PCL polymer).

Process 600 may further include forming the mixed polymer into a filament for 3D printing (block 630), and printing a preform from the filament material using a 3D printer (block 640). For example, the crosslinked copolymer may be extruded into a filament of a standard size (e.g., 1.75 mm or 3 mm diameter) designed to work with a Fused Deposition Modeling (FDM)-based 3D printing platform (e.g., as described below in platform 700). The filament may be fed into the 3D printing platform, which can be programmed to print a desired preform shape, such as one of preforms 100, 200, 300, 400, or 500. In one implementation, the 3D printing platform may execute instructions based on a CAD model to print the desired preform shape.

As described above in connection with FIGS. 1A-5, the shape of the preform and/or the lattice pattern of the preform may be modified to accommodate a particular application. Thus, as shown in the example of preform 100, different cross-sectional thicknesses may be used in a single preform. Additionally or alternatively, as shown in the example of preform 200, a flat layer may be printed with multiple lattice patterns of different densities. In other implementations, as shown in the example of preform 300, a uniform material thickness and density may be used. Thus, preform 100, 200, 300, 400, or 500 may be provided in a single printing process without subsequent steps to add material (e.g., add sections of increased thickness) or remove excess material (e.g., punch out holes to reduce overall preform mass). The 3D printing process is described further below in connection with FIGS. 7 and 8.

Process 600 may also include exposing the printed preform to radiation to modify the polymer chain (block 650). For example, a dose of radiation may be applied to the preform to modify (e.g., crosslink) the polymer chain. Crosslinking of the crosslinking agent and the base PCL polymer may be achieved by, for example, exposing the combined composition to a gamma or electron beam radiation dose sufficient to achieve crosslinking. For the exemplary copolymer composition of be 100 parts PCL, 0.5 parts triallylcyanurate, and 0.5 parts trimethylolpropane trimethacrylate, the radiation dose may generally be between 0.1 to 1.0 Megarads (Mrad) or 1 to 10 Kilogray (kGy) gamma radiation. In one implementation, the radiation exposure may be 0.5 Mrad gamma radiation. In other implementations, the radiation amount required to achieve crosslinking of the printed preform may be less than 0.1 Mrad or greater than 1.0 Mrad for different polymer blends.

While a series of blocks have been described with regard to FIG. 6, the order of the blocks may be modified in other embodiments. For example, in another implementation, the filaments for 3D printing may be exposed to radiation (e.g., radiation sufficient to cause a reaction between the chemical agents and the base material) before they are printed into a preform shape.

Figure 7:
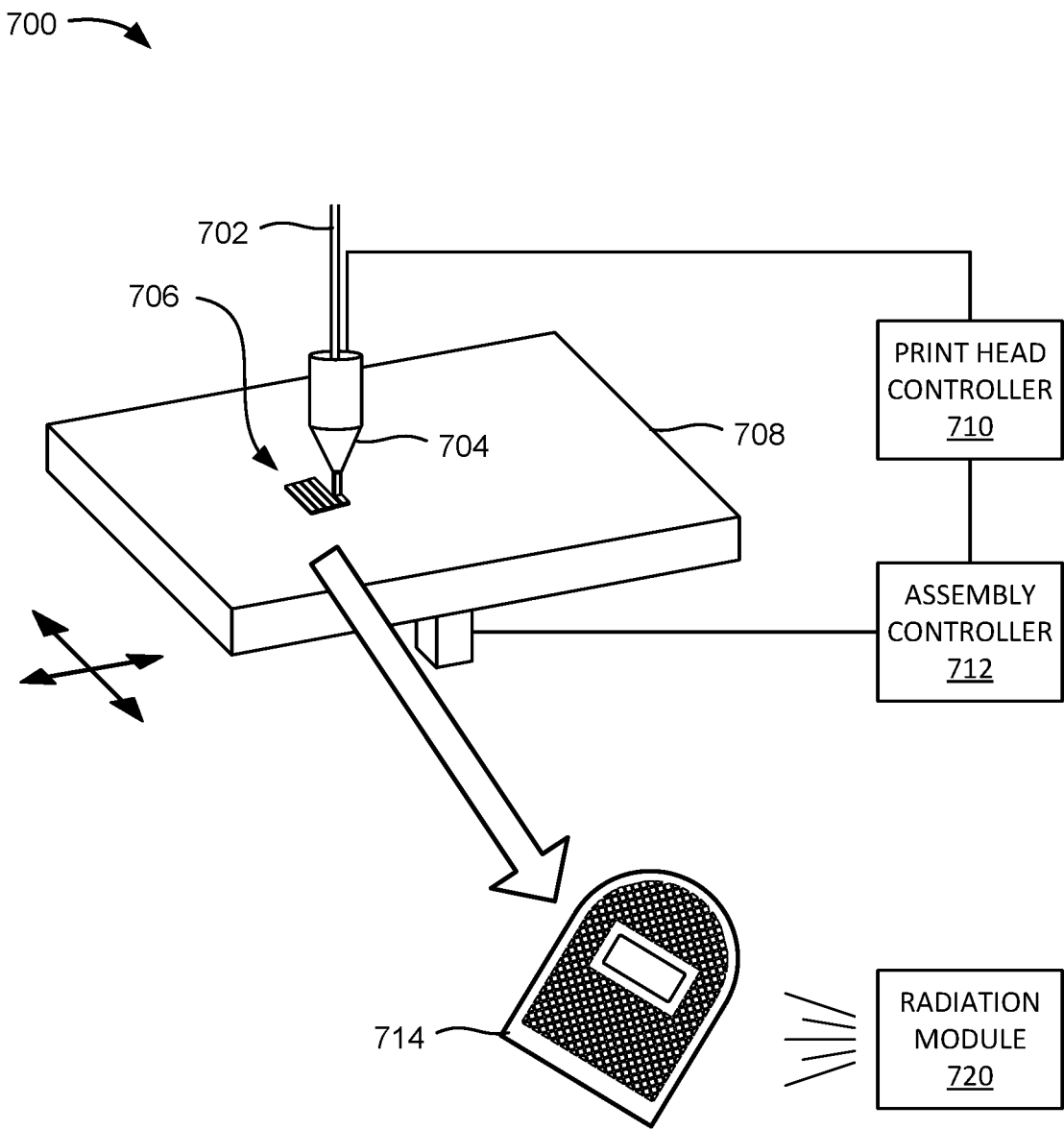
FIG. 7 is a simplified illustration of a preform assembly system.

FIG. 7 provides a simplified illustration of a preform assembly system 700. Use of additive manufacturing techniques, such as 3D printing, in preform assembly system 700 may be used to provide thermoplastic retention device preforms, such as preforms 100, 200, 300, 400, and 500. Using 3D printing, a thermoplastic retention device preform is created from a digital model (e.g., a CAD model) by laying down thermoplastic material in a layer-by-layer fashion. As shown FIG. 7, thermoplastic material promoted with crosslinking agents, in the form of filament 702, is extruded through a heated nozzle 704 and laid out in the desired preform shape. In the example shown in FIG. 7, segments 706 of extruded filament 702 are positioned on a print bed 708. A print head controller 710 and an assembly controller 712 implement instructions in the CAD model to create the desired preform shape. Segments 706 deposited on print bed 708 cool and harden. After multiple passes of nozzle 704, segments 706 accumulate and eventually form the shape of the desired preform indicated in the CAD model.

Print head controller 710 may include logic configured to control nozzle 704. For example print head controller 710 may control heating temperatures and deposition rates of filament 702 through nozzle 704. Assembly controller 712 may control movement of print bed 708 relative to nozzle 704. For example, based on instructions in a CAD model, assembly controller 712 may move print bed 708 to accept segments 706 in a particular arrangement consistent with a desired preform shape. Accumulated segments 706 may deposited on print bed 708 to form preform 714, which may correspond, for example, to any of preforms 100, 200, 300, 400, or 500 described above.

After cooling/hardening, preform 714 may be moved to a radiation module 720 and exposed to radiation sufficient to activate crosslinking agents in preform 714 and modify the polymer chain, as described above with respect to FIG. 6.

Although FIG. 7 shows exemplary components of preform assembly system 700, in other implementations, preform assembly system 700 may include fewer components, different components, differently arranged components, or additional components than the ones depicted in FIG. 7. For example, in another implementation, two or more filaments (e.g., including different polymer blends) may be used to create preform 714 with different material properties in different portions of preform 714. Additionally or alternatively, one or more components of preform assembly system 700 may perform functions described as being performed by one or more other components of preform assembly system 700.

Figure 8:
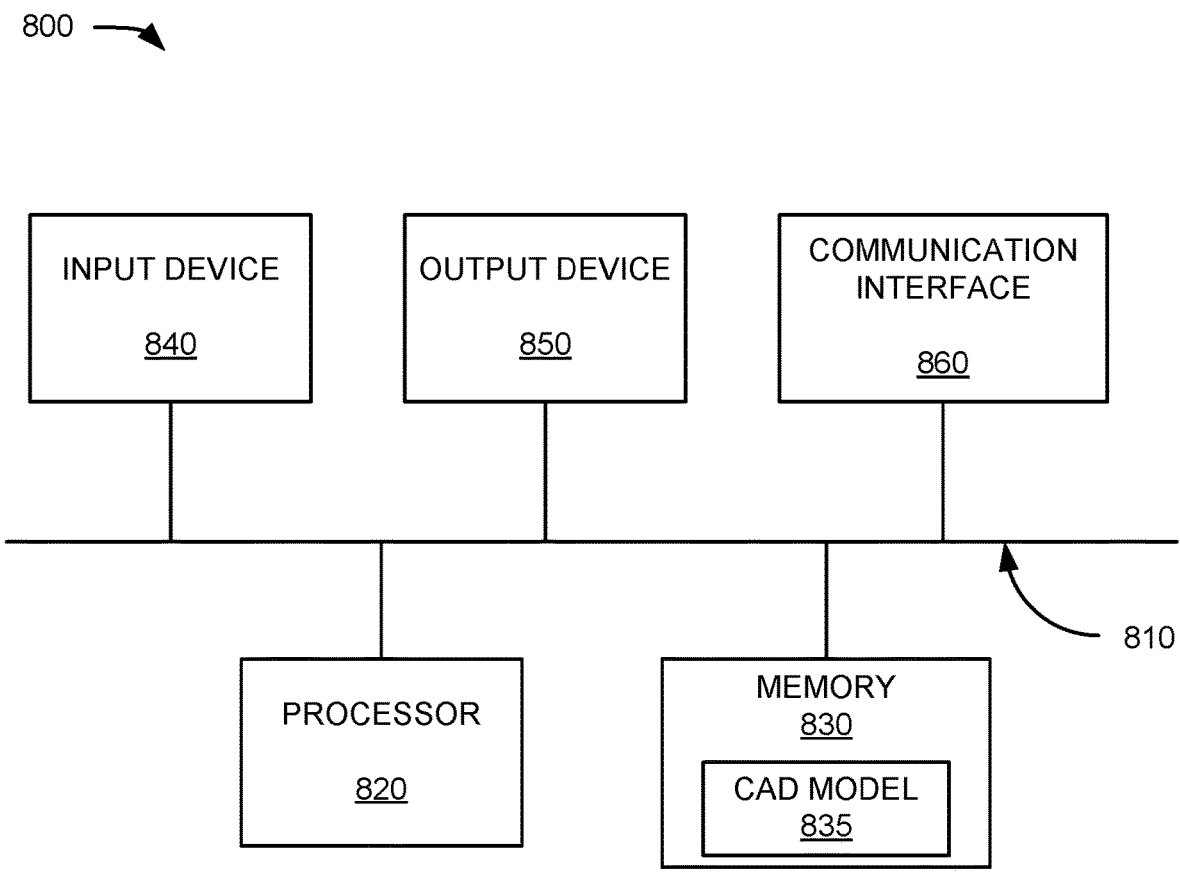
FIG. 8 is a block diagram illustrating exemplary components of a device that may correspond to one or more devices in FIG. 7.

FIG. 8 is a diagram illustrating exemplary components of a device 800. Each of print head controller 710, assembly controller 712, and/or controller for radiation module 720 may include one or more devices 800. As shown in FIG. 8, device 800 may include a bus 810, a processor 820, a memory 830, an input device 840, an output device 850, and a communication interface 860.

Bus 810 may include a path that permits communication among the components of device 800. Processor 820 may include any type of single-core processor, multi-core processor, microprocessor, latch-based processor, and/or processing logic (or families of processors, microprocessors, and/or processing logics) that interprets and executes instructions. In other embodiments, processor 820 may include an application-specific integrated circuit (ASIC), a field-programmable gate array (FPGA), and/or another type of integrated circuit or processing logic.

Memory 830 may include any type of dynamic storage device that may store information and/or instructions, for execution by processor 820, and/or any type of non-volatile storage device that may store information for use by processor 820. For example, memory 830 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

CAD model 835 includes an application or a program that provides a function and/or a process for printing a preform, such as preform 714. In some implementations, CAD model 835 may be incorporated with software, firmware, middleware, microcode, hardware description language (HDL), and/or other form of instruction. By way of example, CAD model 835 may include a CAD model and a corresponding software application (stored in memory 830) which provides instructions for generating a thermoplastic preform.

Input device 840 may allow an operator to input information into device 800. Input device 840 may include, for example, a keyboard, a mouse, a pen, a microphone, a remote control, an audio capture device, an image and/or video capture device, a touch-screen display, and/or another type of input device. Output device 850 may output information to an operator of device 800. Output device 850 may include a display, a printer, a speaker, and/or another type of output device. For example, device 800 may include a display, which may include a liquid-crystal display (LCD) for displaying content to the customer.

Communication interface 860 may include a transceiver that enables device 800 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications.

As described above, device 800 may perform certain operations relating to control of a process for creating thermoplastic preforms using 3D printing. Device 800 may perform these operations in response to processor 820 executing software instructions (e.g., CAD model 835) contained in a computer-readable medium, such as memory 830. A computer-readable medium may be defined as a non-transitory memory device. A memory device may be implemented within a single physical memory device or spread across multiple physical memory devices. The software instructions may be read into memory 830 from another computer-readable medium or from another device. The software instructions contained in memory 830 may cause processor 820 to perform processes described herein. Alternatively, hardwired circuitry may be used in place of, or in combination with, software instructions to implement processes described herein. Thus, implementations described herein are not limited to any specific combination of hardware circuitry and software.

Although FIG. 8 shows exemplary components of device 800, in other implementations, device 800 may include fewer components, different components, additional components, or differently arranged components than depicted in FIG. 8. Additionally or alternatively, one or more components of device 800 may perform one or more tasks described as being performed by one or more other components of device 800.

In implementations described herein, a method for forming a preform for a thermoplastic retention device is provided. A thermoplastic base material is with one or more crosslinking agents to form a polymer blend. The polymer blend is formed into a filament sized for a 3D printing platform, and a preform shape is printed from the filament using the 3D printing platform. The printed preform shape is then exposed to radiation that is sufficient to cause a reaction between the chemical agents and the base material. The radiation causes the chemical agents to modify a polymer chain of the base material, creating a memory in the material.

In contrast with current preforms for thermoplastic retention devices, with the use of 3D printing, the thickness and the lattice pattern of a preform can be varied within a single preform. The pattern density may be changed to suit particular applications (e.g., patient size, age, etc. as needed. In other cases, different materials (e.g., with different material properties) may be printed within a preform to create different desired results including strength concentrations or color variations. In other cases the surface profile of the preform may vary within a single preform, That is, thicker or thinner features may be formed, if desired. In other implementations, the preform may be provided with a three-dimensional, contoured (e.g., non-flat) profile to minimize the amount of deformation required when the preform is formed over a patient.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the scope of the invention.

For example, according to an embodiment of the present invention, a 3D printer may use fused deposition modeling techniques. In other embodiments, extrusion, stereolithography, or any other additive manufacturing technique of producing 3D objects may be used. Thus, implementations described herein are not limited by any 3D printing technology that could be used to produce a 3D preform from a digital file. Furthermore, different features illustrated separately above may be combined in a single embodiment. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A method for forming a preform for a thermoplastic retention device, the method comprising:
   providing a thermoplastic base material including polycaprolactone (PCL);
   blending the base material with one or more chemical agents to form a polymer blend, the one or more chemical agents being configured to modify a polymer chain of the base material when the polymer blend is exposed to radiation;
   forming the polymer blend into a filament sized for a three-dimensional printing platform;
   exposing the filament to radiation sufficient to cause a reaction between the one or more chemical agents and the base material;
   printing a preform shape from the exposed filament using the three-dimensional printing platform; and
   after the printing, and without removing excess material from the preform shape, securing the preform shape to a rigid frame.

2. The method of claim 1, wherein the one or more chemical agents include exactly two trifunctional monomers.

3. The method of claim 2, wherein the one or more chemical agents include triallylcyanurate and trimethylolpropane trimethacrylate.

4. The method of claim 1, wherein the one or more chemical agents include exactly two active crosslinking agents in equal weights.

5. The method of claim 1, wherein the three-dimensional printing platform includes a fused deposition modeling (FDM)-based three-dimensional printer.

6. The method of claim 1, wherein printing the preform shape includes:
   printing the preform shape with a consistent thickness, wherein the preform shape includes a flat base layer area and a reinforcement area, the reinforcement area having an increased pattern density compared to the base layer area.

7. The method of claim 1, wherein printing the preform shape includes:
   printing a base layer having a first thickness, and
   printing a reinforcement layer, having a second thickness, on top of a portion that is less than the entirety of the base layer, wherein the reinforcement layer comprises the same material as the base layer.

8. The method of claim 1, wherein printing the preform shape includes:
   printing a three-dimensional, contoured profile that corresponds to general placement over a particular body feature.

9. The method of claim 1, wherein exposing the filament to radiation includes:
   exposing the filament to between 0.1 to 1.0 Megarads of gamma radiation.

10. The method of claim 1, wherein the rigid frame includes a two-piece structure secured over a portion of the preform.

11. The method of claim 1, wherein printing the preform shape includes:
    printing one or more solid portions and one or more lattice portions within a single layer.

12. The method of claim 1, further comprising
    providing a second thermoplastic base material;
    blending the second thermoplastic base material with one or more of the chemical agents to form a second polymer blend; and
    forming the second polymer blend into another filament sized for the three-dimensional printing platform,
    wherein printing the preform shape comprises printing the preform shape to include material from the filament and the other filament using the three-dimensional printing platform.

13. The method of claim 12, further comprising:
    exposing the other filament to radiation sufficient to cause a reaction between the one or more chemical agents and the second thermoplastic base material,
    wherein the second polymer blend, after the exposing the other filament to radiation, exhibits different material properties than the polymer blend.

14. The method of claim 1, wherein, when exposing the filament to radiation, the reaction lengthens the polymer chain of the base material.

15. The method of claim 1, wherein the thermoplastic base material includes a 50,000 mean molecular weight linear thermoplastic PCL diol polymer.

16. The method of claim 1, wherein the polymer blend includes polycaprolactone (PCL), triallylcyanurate, and trimethylolpropane trimethacrylate.

17. The method of claim 1, wherein exposing the filament to radiation includes:
    exposing the filament to between 0.1 to 1.0 Megarads of gamma radiation.

* * * * *